United States Patent
Ikeda et al.

(10) Patent No.: US 10,667,788 B2
(45) Date of Patent: Jun. 2, 2020

(54) ULTRASOUND IMAGING PICKUP APPARATUS

(71) Applicant: Hitachi, Ltd., Tokyo (JP)

(72) Inventors: Teiichiro Ikeda, Tokyo (JP); Shinta Takano, Tokyo (JP); Hiroshi Masuzawa, Tokyo (JP); Chizue Ishihara, Tokyo (JP); Mayumi Suzuki, Tokyo (JP)

(73) Assignee: HITACHI, LTD., Tokyo (JP)

( * ) Notice: Subject to any disclaimer, the term of this patent is extended or adjusted under 35 U.S.C. 154(b) by 888 days.

(21) Appl. No.: 15/306,880

(22) PCT Filed: Apr. 22, 2015

(86) PCT No.: PCT/JP2015/062303
§ 371 (c)(1),
(2) Date: Oct. 26, 2016

(87) PCT Pub. No.: WO2015/166867
PCT Pub. Date: Nov. 5, 2015

(65) Prior Publication Data
US 2017/0042510 A1 Feb. 16, 2017

(30) Foreign Application Priority Data
Apr. 28, 2014 (JP) ................. 2014-092629

(51) Int. Cl.
*A61B 8/00* (2006.01)
*G01S 7/52* (2006.01)
(Continued)

(52) U.S. Cl.
CPC .............. *A61B 8/4488* (2013.01); *A61B 8/14* (2013.01); *A61B 8/145* (2013.01); *A61B 8/5207* (2013.01);
(Continued)

(58) Field of Classification Search
CPC .. G01S 7/5209; G01S 7/5202; G01S 7/52095; G01S 7/52046; G01S 15/8993;
(Continued)

(56) References Cited

U.S. PATENT DOCUMENTS 8,485,977 B2 7/2013 Hirama
2009/0326377 A1 12/2009 Hirama
(Continued)

FOREIGN PATENT DOCUMENTS

JP 10-277042 A 10/1998
JP 2008-212492 A 9/2008
(Continued)

OTHER PUBLICATIONS

International Search Report of PCT/JP2015/062303 dated Jul. 7, 2015.
(Continued)

*Primary Examiner* — Elmer M Chao
(74) *Attorney, Agent, or Firm* — Mattingly & Malur, PC

(57) ABSTRACT

Reception beamforming is executed using delay times that complexly vary in accordance with differences between transmission conditions. An irradiation area 32 of a transmission beam is calculated, and the lengths of segments, using which delay times are calculated, are set in accordance with the positional relationships between the calculated irradiation area 32 and reception scanning lines 31. For example, the reception scanning lines 31 are divided into areas A to C, and the lengths of segments 40b in the outer area B located outside of the irradiation area 32 are set shorter than the lengths of segments 40a and 40c in the inner areas A and C.

13 Claims, 14 Drawing Sheets

(51) Int. Cl.
  *A61B 8/14* (2006.01)
  *G01S 15/89* (2006.01)
  *G01N 29/26* (2006.01)
  *A61B 8/08* (2006.01)
  *G10K 11/34* (2006.01)

(52) U.S. Cl.
  CPC ......... *A61B 8/5269* (2013.01); *G01N 29/262* (2013.01); *G01S 7/52085* (2013.01); *G01S 15/8915* (2013.01); *G01S 15/8997* (2013.01); *G10K 11/346* (2013.01)

(58) Field of Classification Search
  CPC ....... A61B 8/483; A61B 8/4488; A61B 8/145; A61B 8/5207; A61B 8/14; A61B 8/5269
  See application file for complete search history.

(56) References Cited

U.S. PATENT DOCUMENTS

| | | |
|---|---|---|
| 2010/0030081 A1 | 2/2010 | Masuzawa et al. |
| 2016/0174938 A1 | 6/2016 | Takano |

FOREIGN PATENT DOCUMENTS

| | | |
|---|---|---|
| JP | 2009-240700 A | 10/2009 |
| WO | 2008/108115 A1 | 9/2008 |
| WO | 2015/025655 A1 | 2/2015 |

OTHER PUBLICATIONS

International Preliminary Report on Patentability received in corresponding International Application No. PCT/JP2015/062303 dated Nov. 10, 2016.

FIG. 2
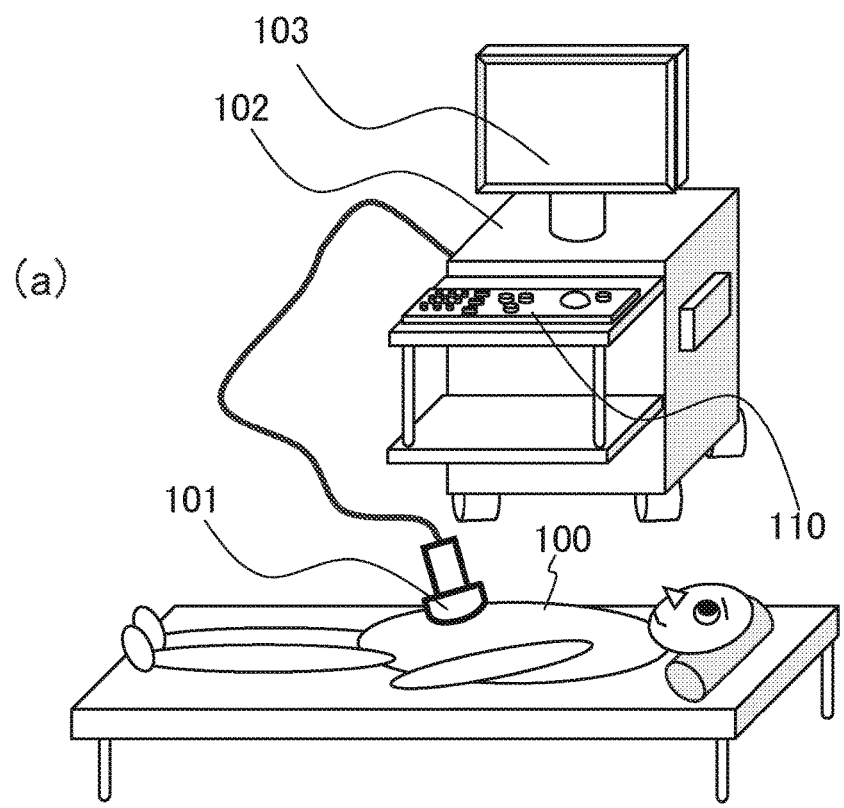
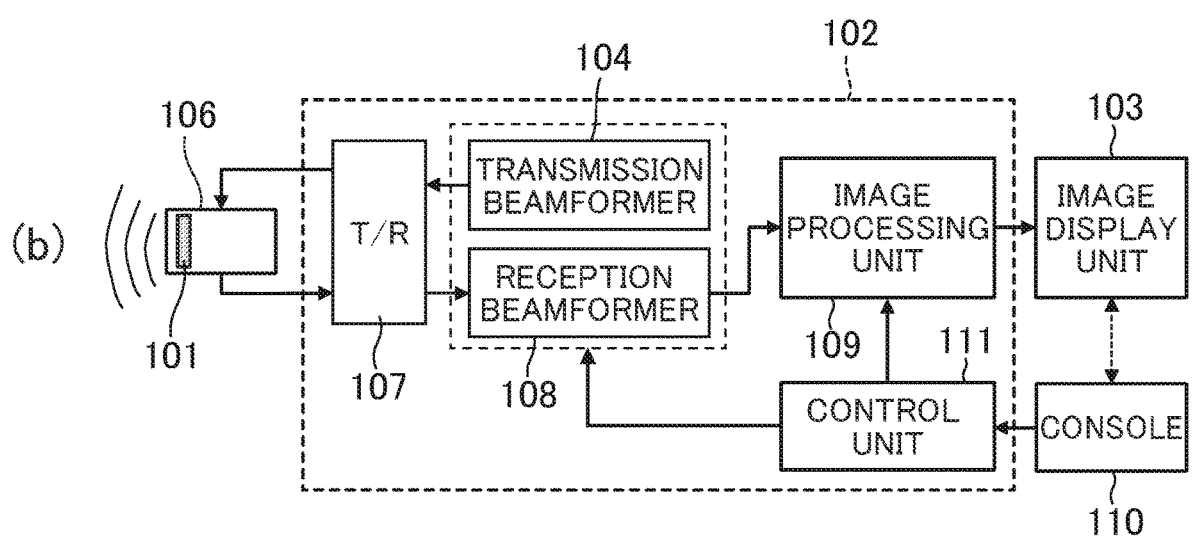

FIG. 5
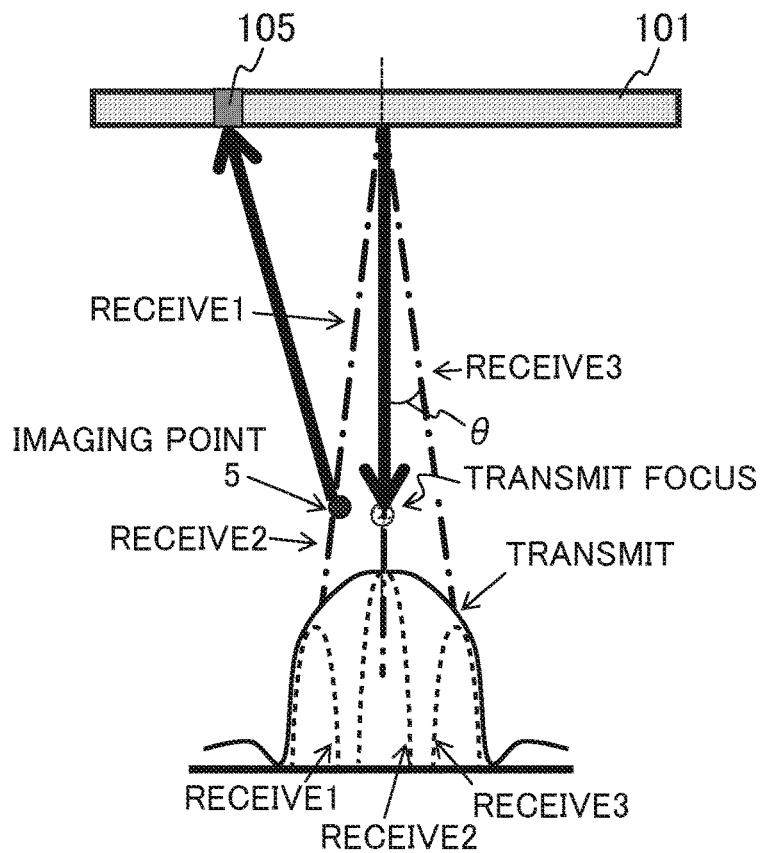
(a)
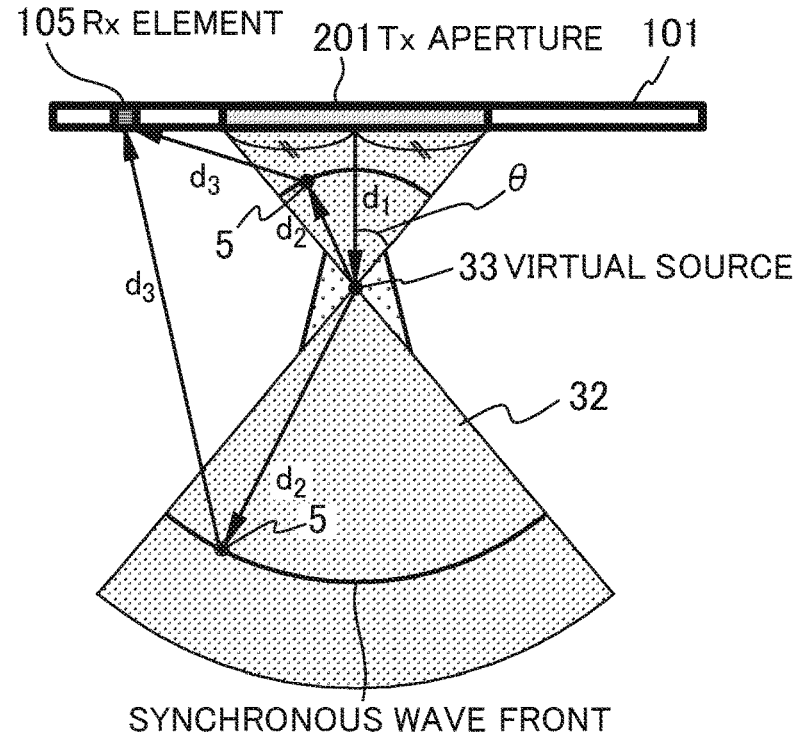
(b)

FIG. 7
(a) 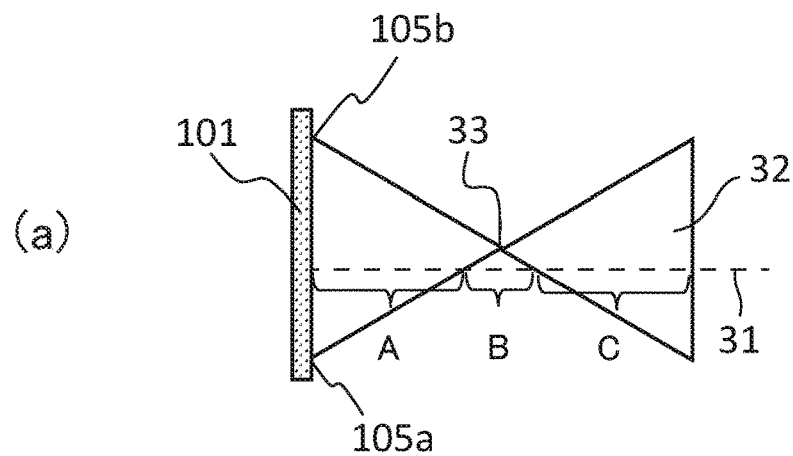
(b) 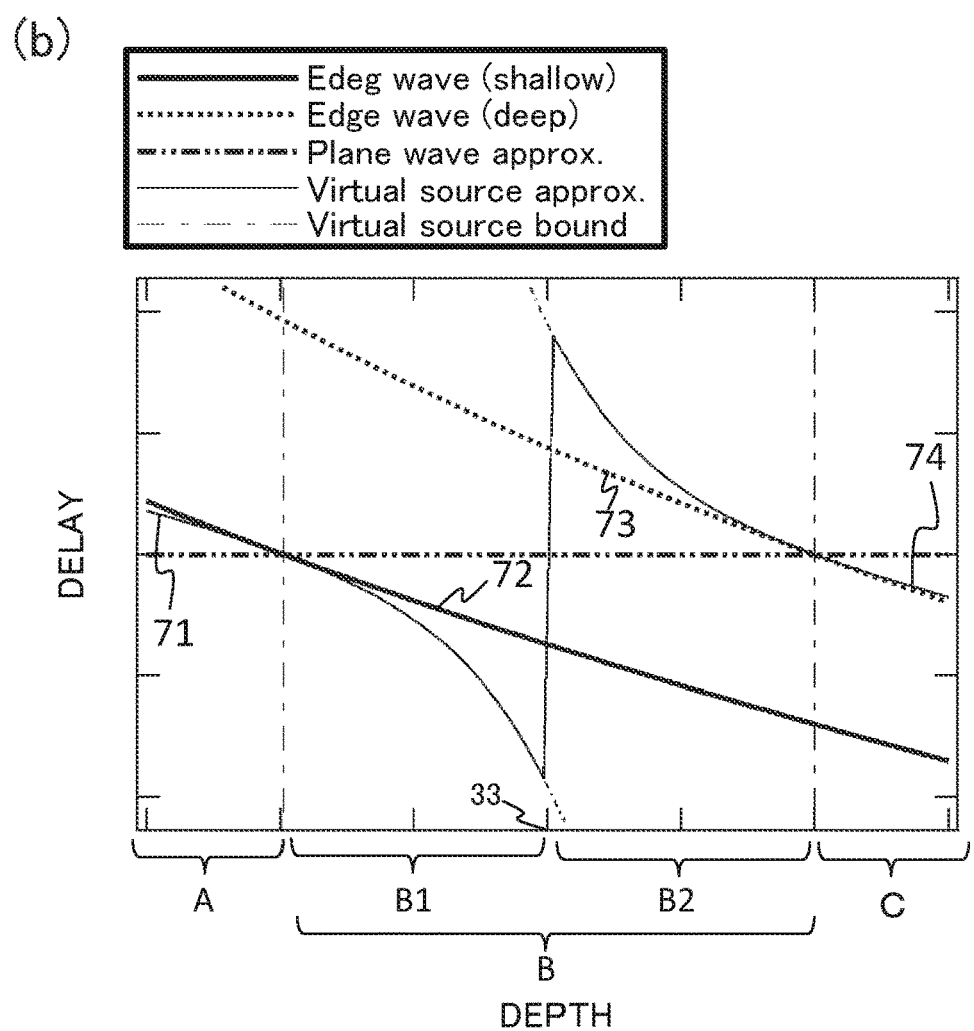

FIG. 8
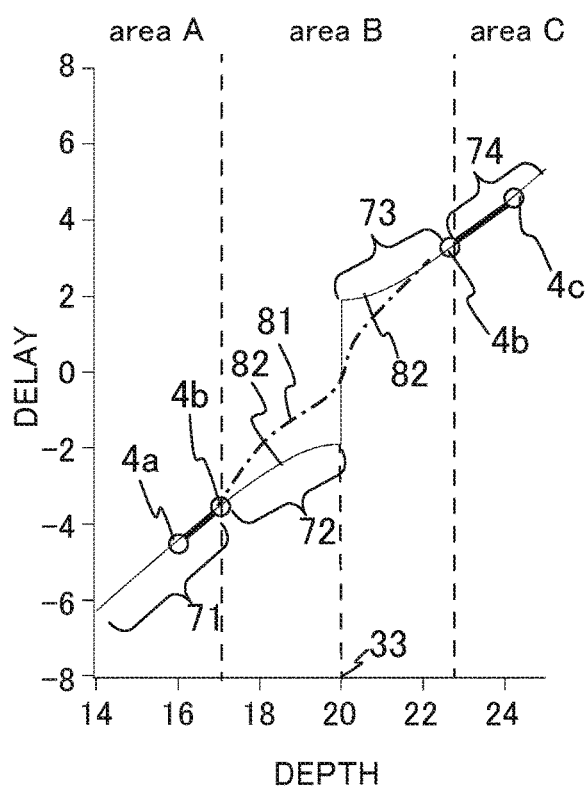
(a)
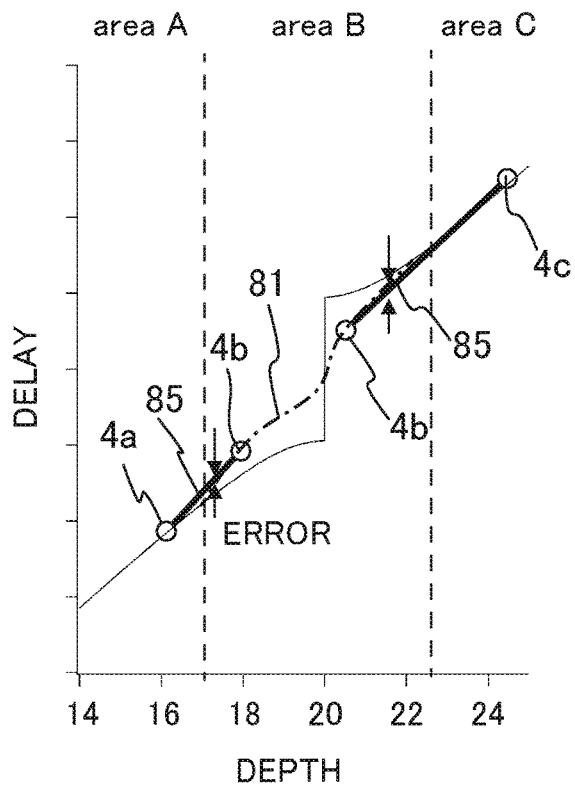
(b)

FIG. 11
(a)
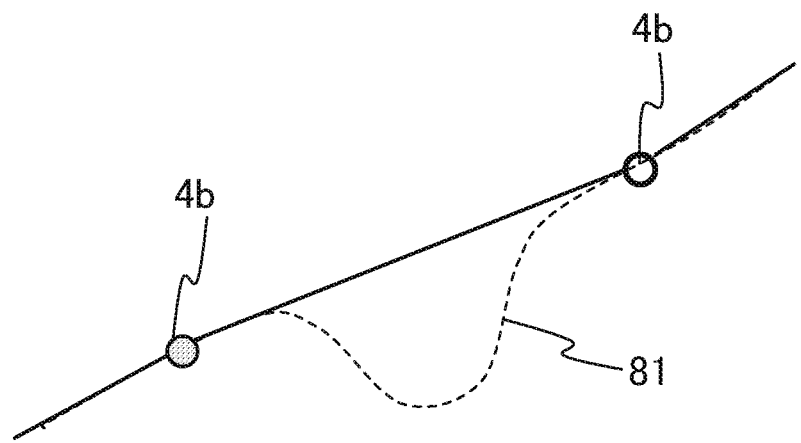
(b)
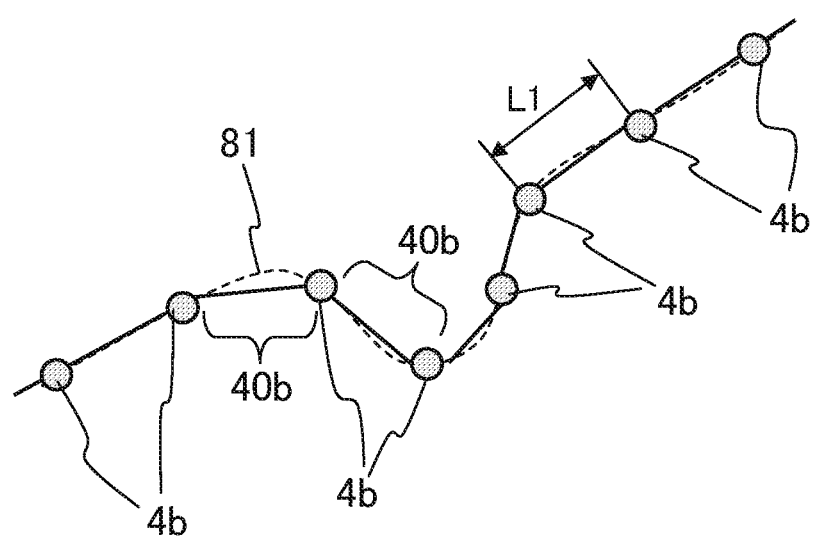

FIG. 13
(a)
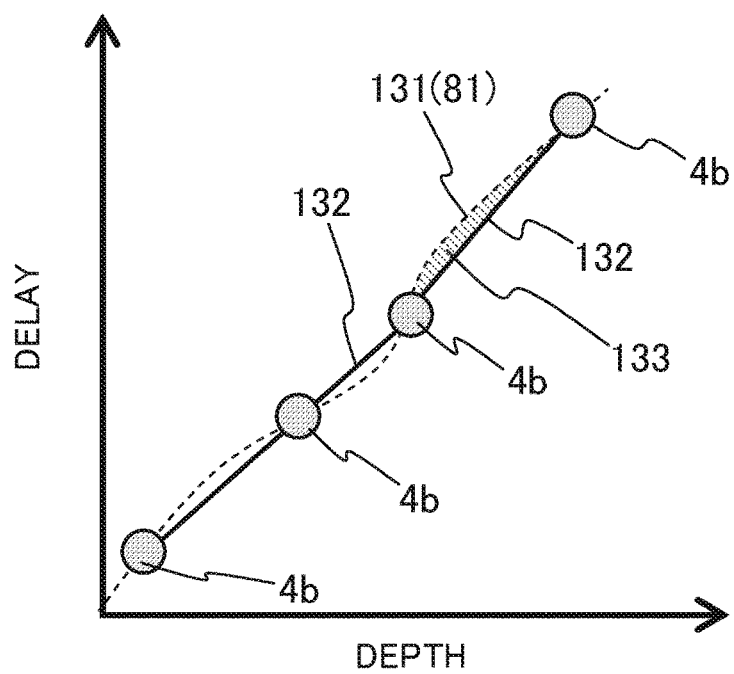
(b)
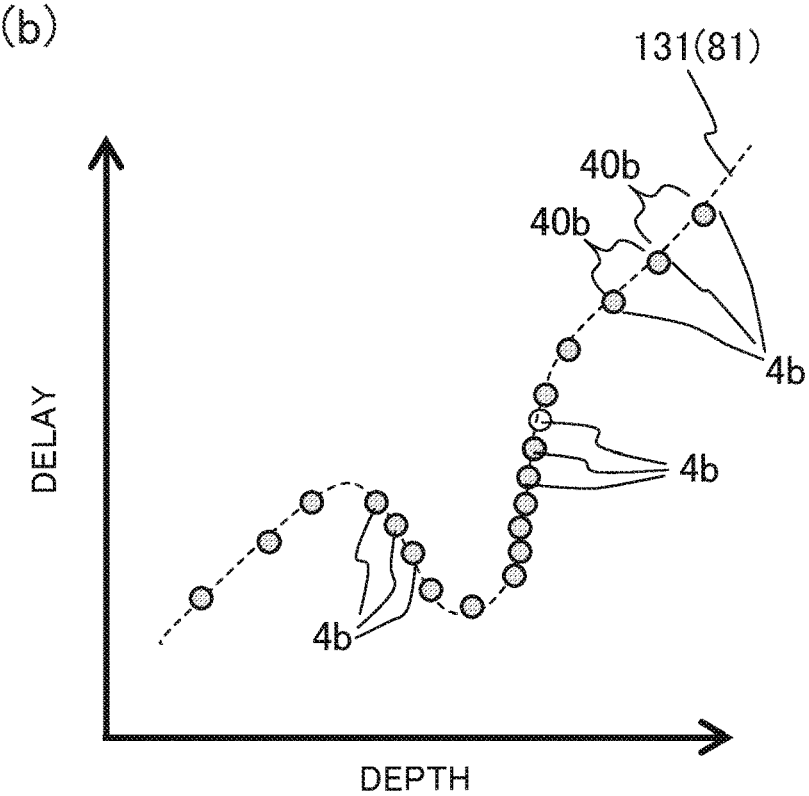

ULTRASOUND IMAGING PICKUP APPARATUS

TECHNICAL FIELD

The present invention relates to an ultrasound imaging technology that takes images inside of a test object using ultrasound waves.

BACKGROUND ART

The ultrasound imaging technology is a technology that takes images of the inside of a test object such as a human body noninvasively using ultrasound waves (inaudible sound waves, that is, sound waves whose frequencies are typically 20 kHz or higher).

As a transmission method for transmitting an ultrasound beam from an ultrasound probe to a test object such as a human body, there are two kinds of transmission methods; one is a dispersing-type transmission method in which an ultrasound beam that disperses in a fan shape is transmitted, and the other is a focusing-type transmission method in which the transmit focus of an ultrasound beam is disposed inside of a test object, and the ultrasound beam is converged on the focus.

Because the transmission or reception of ultrasound waves by an ultrasound image pickup apparatus is performed by means of an array with an aperture of a finite diameter, the transmission or reception is affected by the diffractions of the ultrasound waves caused by the edge of the aperture, therefore it is difficult to improve the resolution in the direction of an azimuthal angle. The above problem can be solved if an array of an infinite length can be prepared, but in actuality it is impossible to prepare an array of an infinite length. Therefore, in order to improve the resolution in the direction of an azimuthal angle, channel domain phasing technologies have been widely studied in recent years, with the result that new phasing schemes such as an adaptive beamformer and aperture synthesis have been extensively reported.

The aperture synthesis will be briefly explained. First, by respectively giving delay times to reception signals received by plural elements included in an ultrasound probe, the delayed reception signals are virtually focused on a certain point, and then a phased signal is obtained by adding these delayed reception signals. The aperture synthesis is performed by synthesizing this phased signal and one phased signal or more obtained regarding the same point through other one or more transmissions or receptions, and by superimposing these signals on each other.

In the aperture synthesis, because phased signals obtained by an ultrasound probe through the transmission or reception to or from different directions regarding a certain point can be superimposed on each other, it can be expected that the improvement of the resolution of a point image and the robustness against the inhomogeneity of the point image are provided. In addition, because processing gain can be increased owing to the superimposing processing, the number of transmissions of ultrasound waves can be reduced in comparison with the number of usual transmissions of ultrasound waves, the aperture synthesis can also be applied to high-speed imaging.

An invention proposed in Patent Literature 1 relates to an ultrasound diagnostic apparatus, and discloses a beamformer in which, during a time interval obtained by partitioning time, beamformer data (delayed data) is calculated using a function, and this time interval is used as a common time interval used for each reception processing condition of the beamformer.

Furthermore, Patent Literature 2 relates to an ultrasound diagnostic apparatus, and discloses a technology in which aperture synthesis is performed using an improved virtual source method in ultrasound imaging in which focusing-type transmission is executed. To put it concretely, the aperture synthesis is performed under the assumption that a focus is a virtual source in an area where the energy of an ultrasound beam is converged on a focus (an area A shown in FIG. 2 of Patent Literature 1), while the aperture synthesis is performed under the assumption that a spherical wave is irradiated from the end of a probe in areas which are adjacent to the area A and in which the energy of the ultrasound beam disperses (areas B and C).

CITATION LIST

Patent Literature

Patent Literature 1: United States Patent Application Publication 2010/0030081 (corresponding to Japanese Unexamined Patent Application Publication No. 2008-212492 and WO 08/108115)
Patent Literature 2: Japanese Unexamined Patent Application Publication. No. Hei10 (1998)-277042

SUMMARY OF INVENTION

Technical Problem

The focusing-type transmission method has smaller errors between delay times even in the case where the divergence angle of transmission is large in comparison with the dispersing-type transmission method. Therefore, in the focusing-type transmission method, because the divergence angle of the transmitted ultrasound wave can be set large, a larger number of reception scanning lines (assemblies of points at which phased signals are calculated) can be set in comparison with in the dispersion-type transmission method. It becomes possible to speedily image a wider imaged area with a fewer number of transmissions by setting a many number of reception scanning lines. In addition, in transmission aperture processing, more phased signals can be synthesized in the case of a large number of reception scanning lines being set than in the case of a small number of reception scanning lines being set even if the same number of transmissions are executed in both cases, and advantageous effects such as the improvement of resolution can be obtained.

Furthermore, as shown in Patent Literature 2, delay times are calculated in the irradiation area of a transmission beam (in an area where ultrasound energy is converged) using the virtual source method, and delay times are calculated under the assumption that a spherical wave is irradiated from the end of a probe outside of the irradiation area of the transmission beam areas where the energy of the ultrasound beam disperses), which makes it possible to obtain phased signals even at points outside of the irradiation area of the transmission beam. Therefore, reception scanning lines can be set even outside of the irradiation area of the transmission beam.

However, in the case where delay times at points on a reception scanning line outside of the irradiation area of the transmission beam are calculated using the waveform of a spherical wave which is considered to be irradiated from the end of the probe according to the technology disclosed in Patent Literature 2, the waveform of the spherical wave used for calculation of the delay times have to be switched from the waveform f a spherical wave irradiated from the left part of the edge of the probe to the waveform of a spherical wave irradiated from the right part of the edge of the probe or vice versa in the vicinity of the depth of a transmit focus. Owing to this switching, there arises a problem in that a curve representing the variation between delay times in the direction of the depth along the reception scanning line becomes discontinuous in the vicinity of the depth of the transmit focus. Unless the discontinuity of the variation between the delay times in the vicinity of the depth of the transmit focus is approximated by some kind of approximating curve or another to change the discontinuous curve into a continuous curve, the pixel values of an ultrasound image to be generated become discontinuous in the vicinity of the depth of the transmit focus, so that an artifact is generated. In this case, such an approximating curve has to have a complex shape including one or more inflection points to continuously connect the discontinuous variation between the delay times.

On the other hand, because a typical ultrasound image pickup apparatus has a limited calculation capacity, delay times regarding all reception phasing points (sampling points at the time of phasing of reception signals) on the reception scanning line cannot be calculated using the virtual source method or using the waveform of a spherical wave. Therefore, after setting segments whose lengths are longer than the distance between the reception phasing points on the reception scanning line, delay times are calculated regarding only nodes between the segments using the virtual source method or using the waveform of a spherical wave. Next, delay times regarding reception phasing points within a segment are calculated using linear interpolation calculation or the like with reference to delay times at the nodes of the both ends of the segment. Herewith, the calculation amount of delay times can be controlled, and the high-speed display of the ultrasound images can be realized.

Therefore, in the case where delay times at reception phasing' points in the vicinity of the depth of a transmit focus are intended to be calculated using the technology disclosed in the abovementioned Patent Literature 2, if distances between segments are large, it is impossible to set delay times, in which the change of the abovementioned approximating curve is reflected, at the reception phasing points using interpolation calculation. In addition, although the shape of the curve of delay times at reception phasing points complexly varies depending on a transmission condition and the position of a reception scanning line, if the lengths of segments are large, the interpolation calculation cannot cope with the change of the shape of the curve of the delay times. Therefore, image qualities in the vicinity of the depth of the transmit focus become deteriorated.

One of the objects of the present invention is to execute reception beamforming using delay times that complexly vary depending on differences between transmission conditions.

Solution to Problem

An ultrasound image pickup apparatus according to the present invention includes a reception beamformer in which the irradiation area of a transmission beam is calculated, and the lengths of segments on a reception scanning line are determined in accordance with the shape of the calculated irradiation area, wherein each of the segments includes one or more reception phasing points and is used for the calculation of delay times.

For example, the ultrasound image pickup apparatus according to the present invention includes: an ultrasound element array in which plural ultrasound elements are arranged in a predefined direction; a transmission beamformer that makes at least some of the plural ultrasound elements transmit a focusing-type transmission beam to the imaged area of a test object; a reception beamformer that delays reception signals output by plural ultrasound elements, which receive ultrasound waves from the test object, by delay times to phase the reception signals, and adds the phased reception signals; and an image processing unit that generates image data using phased signals output by the reception beamformer. The reception beamformer includes: a segment setting unit that sets plural reception scanning lines, each of which is an assembly of reception phasing points, in the imaged area, and divides each of the reception scanning lines into plural segments; a delay time calculation unit that calculates delay times at the positions of the nodes of the plural segments, which are set by the segment setting unit, using a predefined calculation method; a delaying/phasing unit that calculates a delay time at at least one reception phasing point included in each of the segments using delay times at the nodes of the segment, and delays a reception signal at the at least one reception phasing point by the calculated delay time; and a transmission area calculation unit that calculates an irradiation area in the imaged area of the focusing-type transmission beam transmitted by the transmission beamformer. The segment setting unit sets the lengths of the plural segments respectively in accordance with the positional relationships between the shape of the irradiation area calculated by the transmission area calculation unit and the reception scanning lines.

Advantageous Effects of Invention

According to the present invention, because reception beamforming can be executed using delay times that complexly vary in accordance with differences between transmission conditions, an ultrasound image whose quality is prevented from being deteriorated can be generated.

BRIEF DESCRIPTION OF DRAWINGS

FIGS. 2(a) and (b) are a perspective view and a block diagram of the ultrasound image pickup apparatus of the first embodiment respectively.

FIG. 5(a) is an explanatory diagram for explaining beamforming by means of a dispersing-type transmission beam, and (b) is an explanatory diagram for explaining beamforming by means of a focusing-type transmission beam.

FIG. 7 (a) is an explanatory diagram showing that a reception scanning line 31 is divided into areas A to C depending on the positional relationship between the reception scanning line 31 and the irradiation area 32 of a transmission beam, and (b) is a graph showing the curves of delay times calculated from the wave fronts in the respective areas A to C.

FIG. 8(a) is a graph showing an approximating curve 81 that connects the curves of delay times calculated from the wave fronts, and (b) is an explanatory diagram showing the disjunctions between the approximating curve 81 and line segments that connect segment nodes.

FIG. 11 (a) is an explanatory diagram showing the relationship between a line segment that connects segment nodes and a curve 81 in the case of the length of the segment being set large, and FIG. 11(b) is an explanatory diagram showing the relationships between line segments that connect segment nodes and curves 81 in the case of the lengths L1 of the segments being set small.

FIG. 13(a) is an explanatory diagram showing the areas of areas between line segments that connect the segments nodes 4b of the third embodiment and a curve 131, and (b) is an explanatory diagram showing that the lengths of segments are set in accordance with the gradient of a curve 131 in the second embodiment.

DESCRIPTION OF EMBODIMENTS

Hereinafter, an ultrasound image pickup apparatus of one embodiment according to the present invention will be explained.

First Embodiment

Figure 1:
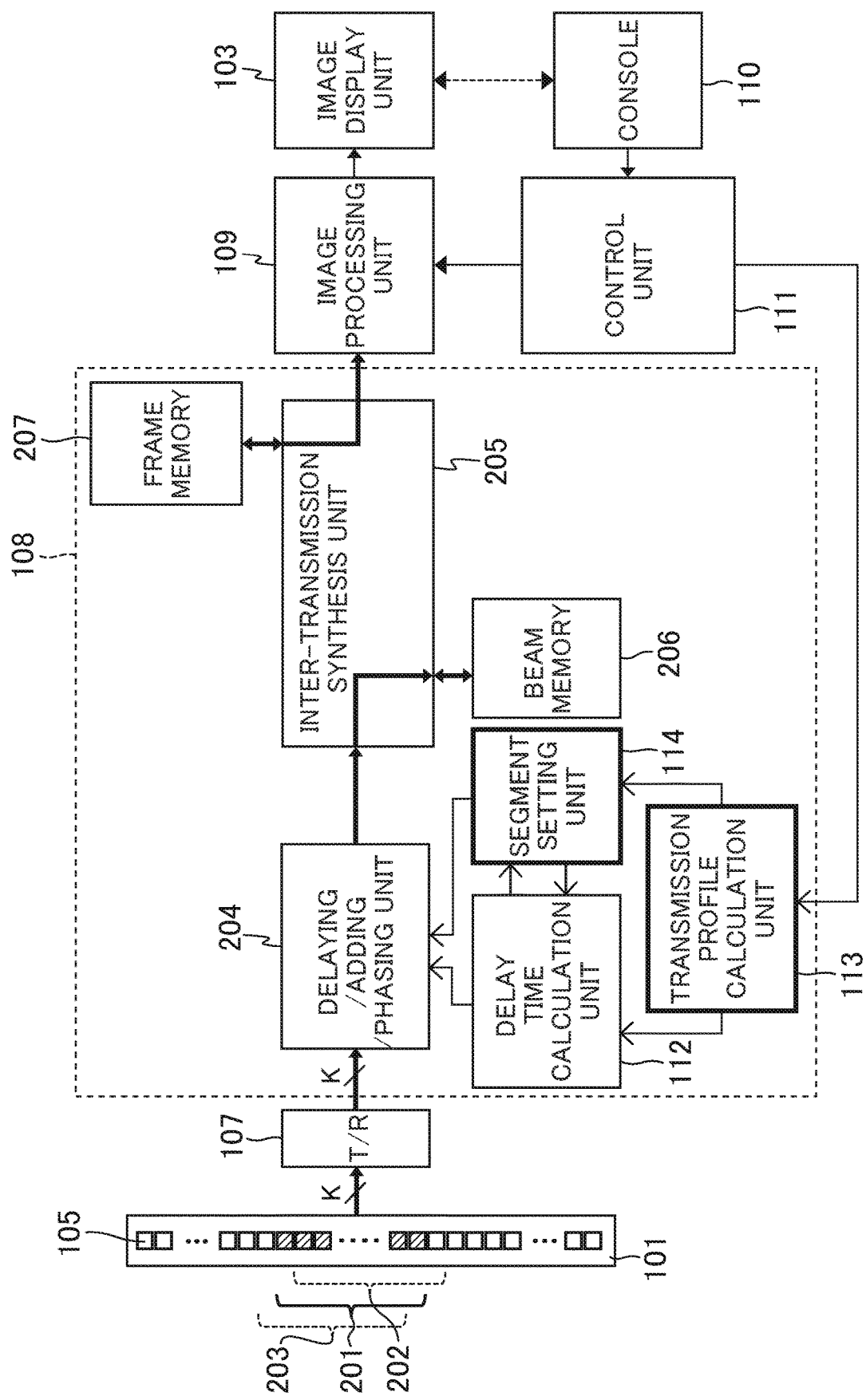
FIG. 1 is a block diagram showing the configuration of the reception beamformer of an ultrasound image pickup apparatus of a first embodiment.

An ultrasound image pickup apparatus of a first embodiment will be explained with reference to FIG. 1, FIGS. 2(a) and (b). FIG. 1 is a block diagram showing a part of the apparatus, FIG. 2(a) is a perspective view of the apparatus, and FIG. 2(b) is a block diagram showing the schematic configuration of the entirety of the apparatus.

As shown in FIG. 1, FIGS. 2(a) and (b), the ultrasound image pickup apparatus of the first embodiment includes: an ultrasound element array 101 in which plural ultrasound elements 105 are arranged in a predefined direction; a transmission beamformer 104 that makes at least a part (201, 202, and 203) of the plural ultrasound elements 105 transmit a focusing-type transmission beam to the imaged area of a test object 100; a reception beamformer 108 that delays reception signals output by the plural of ultrasound elements 105, which receive ultrasound waves from the test object 100, by delay times to phase the reception signals, and adds the phased reception signals; and an image processing unit 109 that generates image data using phased signals output by the reception beamformer 108.

Figure 3:
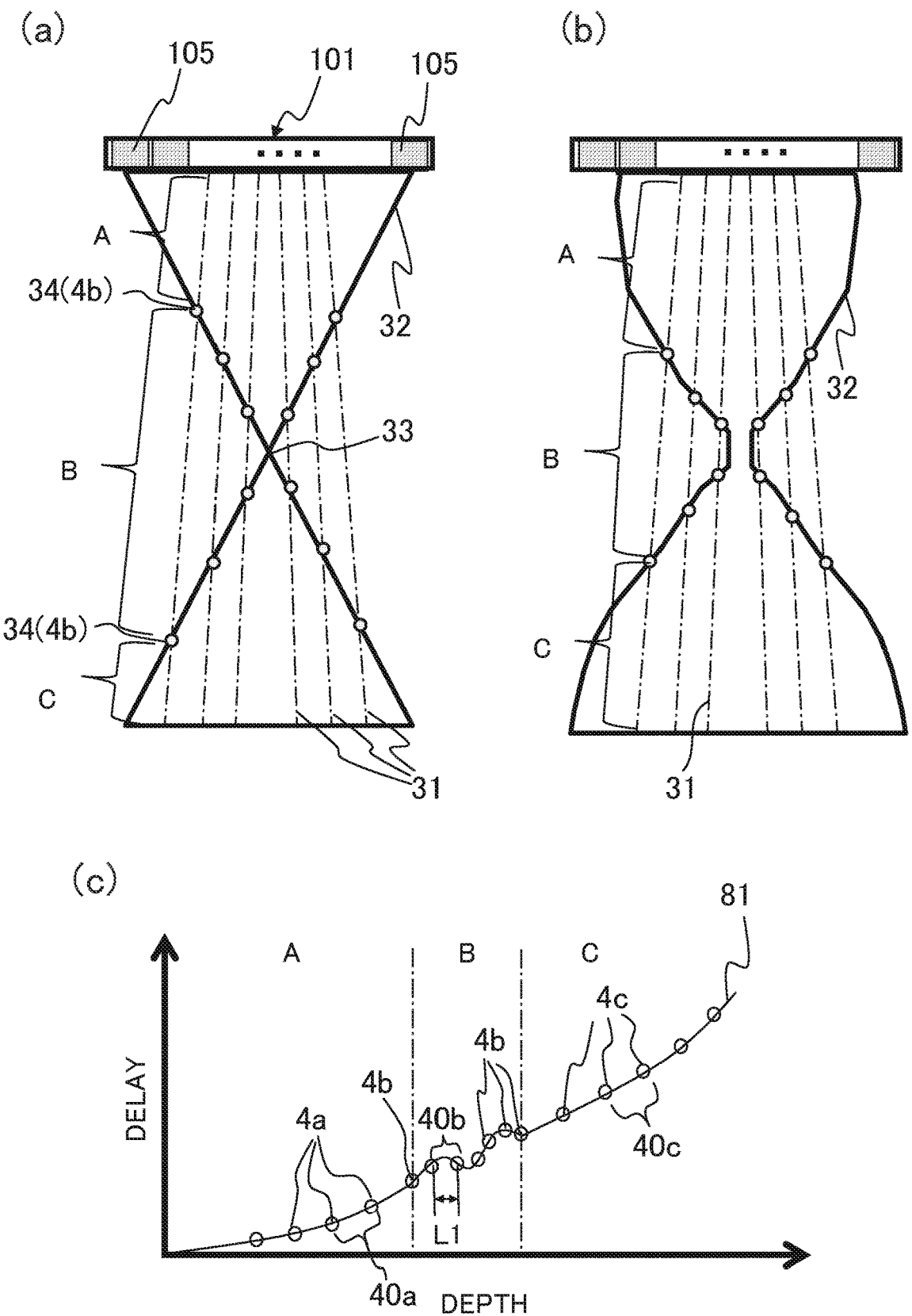
FIGS. 3(a) and (b) are explanatory diagrams showing the relationships between the irradiation area 32 of a transmission beam and reception scanning lines of the first embodiment, and (c) is a graph that shows a curve 81 of the variation between delay times on reception scanning lines and disposal example of segment nodes.

As shown in FIG. 1, the reception beamformer 108 includes a segment setting unit 114, a delay time calculation unit 112, a delaying/phasing unit 204, and a transmission area calculation unit 113. The segment setting unit 114 sets plural reception scanning lines 31, each of which is an assembly of reception phasing points, in the imaged area as shown in FIGS. 3(a) and (b), and divides each of the reception scanning lines 31 into plural segments 40a, 40b, and 40c as shown in FIG. 4(a). The delay time calculation unit 112 calculates delay times at the positions of the nodes 4a, 4b, and 4c of the plural segments 40a, 40b, and 40c, which are set by the segment setting unit 114, using a predefined calculation method. The delaying/phasing unit 204 calculates the delay time of a reception signal at each of predefined reception phasing points 5 on the segments 40a, 40b, and 40c of a reception scanning line 31 using the delay times at the nodes 4a, 4b, and 4c of the segments calculated by the delay time calculation unit 112. Then the delaying/phasing unit 204 delays the reception signals at the reception phasing points 5 by the calculated delay times to phase the reception signals Here, so-called reception phasing points are points at which phased signals for reception signals are calculated, and the reception phasing points correspond to the imaging points of an ultrasound image, and/or correspond to the sampling points at the time of phasing the reception signals.

The transmission area calculation unit 113 calculates an irradiation area 32 in the imaged area of the focusing-type transmission beam transmitted by the transmission beamformer 104. The segment setting unit 114 sets the lengths of the plural segments 40a, 40b, and 40c respectively in accordance with the positional relationships between the shape of the irradiation area 32 calculated by the transmission area calculation unit 113 and the reception scanning lines 31.

Figure 4:
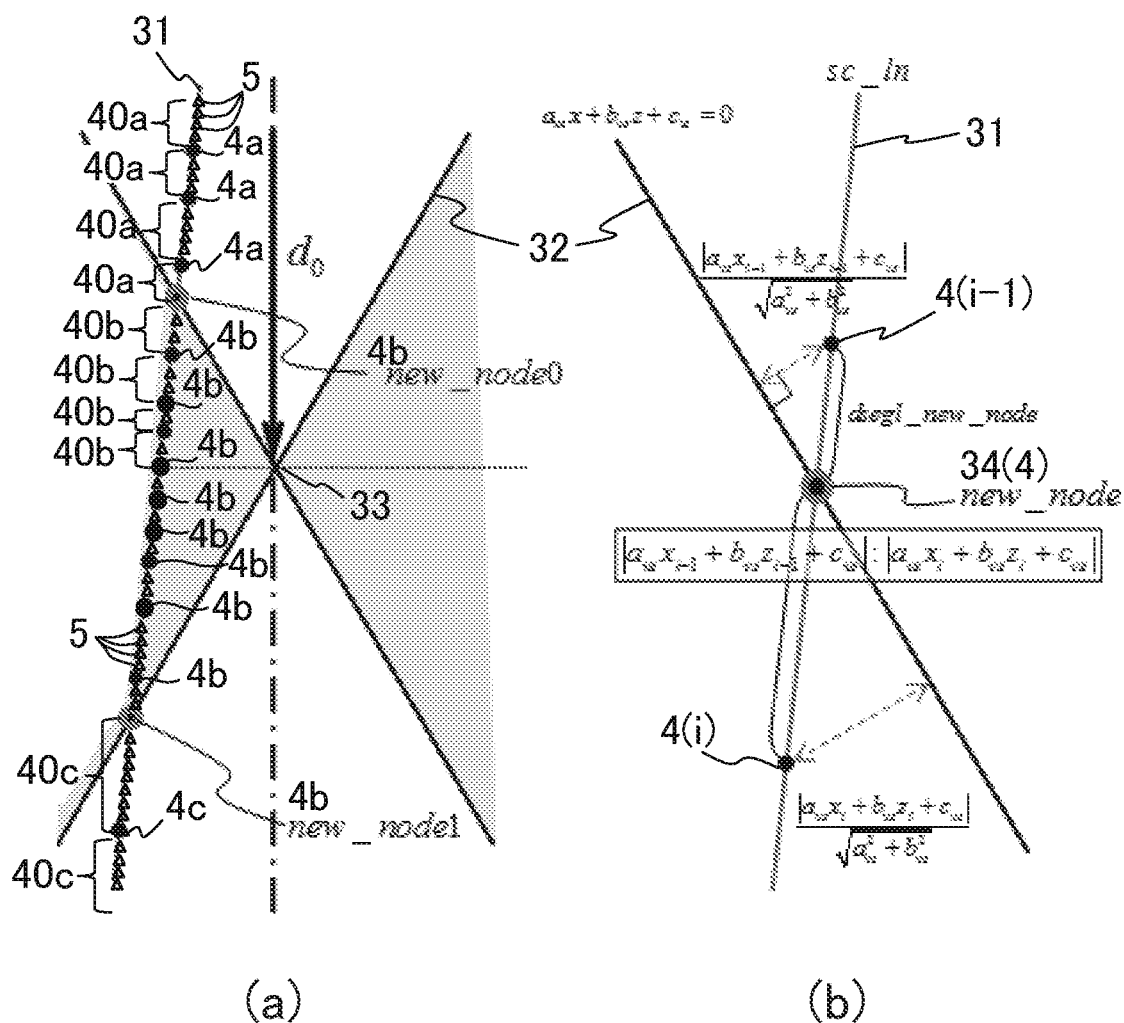
FIG. 4(a) is an explanatory diagram showing the relationship between the irradiation range 32 of the transmission beam, a reception scanning line 31, segment nodes 4a and the like of the first embodiment and reception phasing points 5 of the first embodiment, and (b) is an explanatory diagram showing how to calculate the position of an intersection point 34 of the irradiation area 32 and the reception scanning line 31 using the positions of two segment nodes.

To put it concretely, as shown in FIGS. 3(a) and (b), the segment setting unit 114 calculates an outer area. B located outside of the irradiation area 32 among the reception scanning lines 31, and inner areas A and C located inside of the irradiation area 32 among the reception scanning lines 31. Then, as shown in FIG. 4, the segment setting unit 114 sets the length of at least one segment among the plural segments 40b to be set in the outer area B shorter than the length of at least one segment among the segments 40a and 40c to be set in the inner areas A and C located inside of the irradiation area 32 among a reception scanning line 31.

Herewith, as shown in FIG. 3(c), even if the shape of the irradiation area 32 makes the variation between delay times complexly vary in the vicinity of the depth of a transmit focus 33, the variation between the delay times can be reflected in delay times at the nodes 4b of segments 40b that have short segment lengths. Therefore, even if the delaying/phasing unit 204 calculates delay times at sample points 5 from the nodes 4b of the segments 40b using interpolation calculation such as linear interpolation or the like, the complex variation between the delay times can be followed. As a result, more accurate phased signals can be generated in the vicinity of the transmit focus 33 in this case than in the case where segments of equal length are set on the entirety of the reception scanning line 31. Furthermore, by setting the length of at least one segment of segments 40*a*, 40*b*, and 40*c* in the inner areas A and C larger than the lengths of segments in the outer area B, the calculation amount necessary for calculating delay times on the whole can be prevented from increasing.

With such a setting, because highly accurate delay times at the reception phasing points can be set even in the outer area B outside of the irradiation area 2, even if many reception scanning lines 31 are set outside of the irradiation area 32 of the transmission beam, highly accurate phased signals can be obtained. It becomes possible to execute aperture synthesis between plural transmissions without increasing the number of transmissions.

For example, as shown in FIG. 1, the reception beamformer 108 includes a beam memory 206 that stores phased signals at reception phasing points 5 generated by the delaying/phasing unit 204 for each transmission, and an inter-transmission synthesis unit 205 that reads out phased signals at the same reception phasing points 5 regarding different transmissions among the phased signals stored in the beam memory 206, and synthesizes the read-out phased signals. In such a way, the aperture synthesis can be executed.

Hereinafter, the ultrasound image pickup apparatus of the first embodiment will be explained more concretely.

The entire configuration of the ultrasound image pickup apparatus will be explained more detailedly with reference to FIG. 1, FIGS. 2(*a*) and (*b*).

As shown in FIG. 2(*a*), the ultrasound image pickup apparatus includes an ultrasound probe 106; an apparatus body 102; an image display unit 103; and a console 110. As shown in FIG. 2(*b*), the transmission beamformer 104; a transmission/reception separation circuit (T/R) 107; the reception beamformer 108; the image processing unit 109; and a control unit 111 that controls the operations of these components are disposed in the apparatus body 102.

As shown in FIG. 1, the reception beamformer 108 includes: the abovementioned delaying/phasing unit (referred to as the delaying/adding/phasing unit hereinafter) 204; the delay time calculation unit 112; the transmission area calculation unit (referred to as the transmission profile calculation unit hereinafter) 113; the segment setting unit 114; the beam memory 206; the inter-transmission synthesis unit 205; and a frame memory 207 as well. Each of the delay time calculation unit 112, the segment setting unit 114, and the transmission profile calculation unit 113 includes a processing unit such as a CPU and a memory, and the processing unit reads a program stored in advance in the memory and executes the program, which makes it possible to configure these units in such a way that the operations of these units explained later are realized. In addition, as an alternative other than this configuration, a configuration that realizes operations explained later is utilizable in which the delay time calculation unit 112, the segment setting unit 114, and the transmission profile calculation unit 113 are formed by means of hardware circuits that execute predefined processes (such as an ASIC and an FPGA), and a register and a memory that store predefined numerical values.

The transmission beamformer 104 shown in FIG. 2(*b*) generates a transmission beam signal for generating an ultrasound transmission beam. The transmission beam signal is transferred to the ultrasound probe 106 via the transmission/reception separation circuit 107. The ultrasound probe 106 transfers the transmission beam signal to the respective ultrasound elements 105 of the ultrasound element array 101. The respective ultrasound elements 105 transmit ultrasound waves to the inside of the body of the test object 100. Echo signals reflected in the body are received by the ultrasound element array 101 of the ultrasound probe 106. The received signals pass through the transmission/reception separation circuit 107 again, and phasing/adding calculation processing and the like are executed on the received signals by the reception beamformer 108.

Before the detailed operations of the respective units of the reception beamformer 108 are explained, beamforming executed by means of a typical dispersing-type transmission beam and beamforming executed by means of a typical focusing-type transmission beam will be explained.

FIG. 5(*a*) is a diagram for explaining beamforming by means of an existing dispersing-type transmission beam. In the case where the divergence angle θ of the dispersing-type transmission beam is small, there is not a large difference between the flight travel of an ultrasound wave transmitted from the outermost side of the transmission beam and the flight travel of an ultrasound wave transmitted in the direction of the transmission sound axis. However, in the case where the divergence angle θ of the transmission beam is large, a difference between the flight travel of an ultrasound wave transmitted from the outermost side of the transmission beam and the flight travel of an ultrasound wave transmitted in the direction of a transmission sound axis becomes large. Therefore, because the divergence angle θ of the dispersing-type transmission beam cannot be set very large, it is difficult to set necessary and sufficient number of scanning lines for high-speed imaging and aperture synthesis.

On the other hand, FIG. 5(*b*) is a diagram for explaining the beamforming by means of a focusing-type transmission beam. In the irradiation area of the focusing-type transmission beam (an area where ultrasound energy is converged) 32, delay times are calculated using the virtual source method. The procedure for calculating the time of flight (TOF) of a sound wave using the virtual source method will be explained with reference to FIG. 5(*b*). The virtual source method is performed under the assumption that a sound wave is reirradiated in a spherical dispersion fashion from the position of a transmit focus that is regarded as a virtual source. For example, in the case of FIG. 5(*b*), the sound wave travels in the direction of the far side from the virtual source, and travels back in time and returns in the direction of the near side to the ultrasound elements. Here, assuming that the origin of time (zero time) in the calculation of time of flight is set as the time when a sound wave is transmitted from the center position of the transmission aperture (201) of the ultrasound element array 101 (the center between elements in the case where the number of the elements in the transmission aperture are even), then the time of flight tof from the time when the sound wave is transmitted to the time when the sound wave reaches a certain ultrasound element 105 after being reflected at an imaging point (a reception phasing point 5) is given by the next Expression (1). In this Expression, $d_1$ is a distance from the center of the transmission aperture to the virtual source (a focal distance in the case of the focusing-type transmission); $d_2$ is a distance from the virtual source to the reception phasing point 5; $d_3$ is a distance between the reception phasing point 5 and the reception ultrasound element 105; and C is the speed of sound in a medium. In Expression (1), the sign "−" of the double sign ± is adopted in the case where the reception phasing point 5 is at the side of the ultrasound element array 101 viewed from the virtual source, and the sign "+" of the double sign ± is adopted in the case where the reception phasing point 5 is at the opposite side of the ultrasound element array 101 viewed from the virtual source. Here, all the distances d in Expression (1) are scalars.
[Expression 1]

$$\text{tof} = (d_1 \pm d_2 + d_3)/C \quad (1)$$

Sign −: in the case where the imaging point is in a transmission irradiation area at the side of the probe.

Sign +: in the case where the imaging point is in a transmission irradiation area at the opposite side of the probe.

Using the virtual source method makes it possible that reception Phasing points 5 are set throughout the entire irradiation area 32 of the transmission beam, and a time of flight for each reception ultrasound element 105 is calculated. Furthermore using the calculated times of flight as delay times makes it possible to execute phasing processing. Therefore, in the focusing-type transmission beam, the divergence angle can be set large, and the width of an area within which the sound wave is propagated can be broadened.

Figure 6:
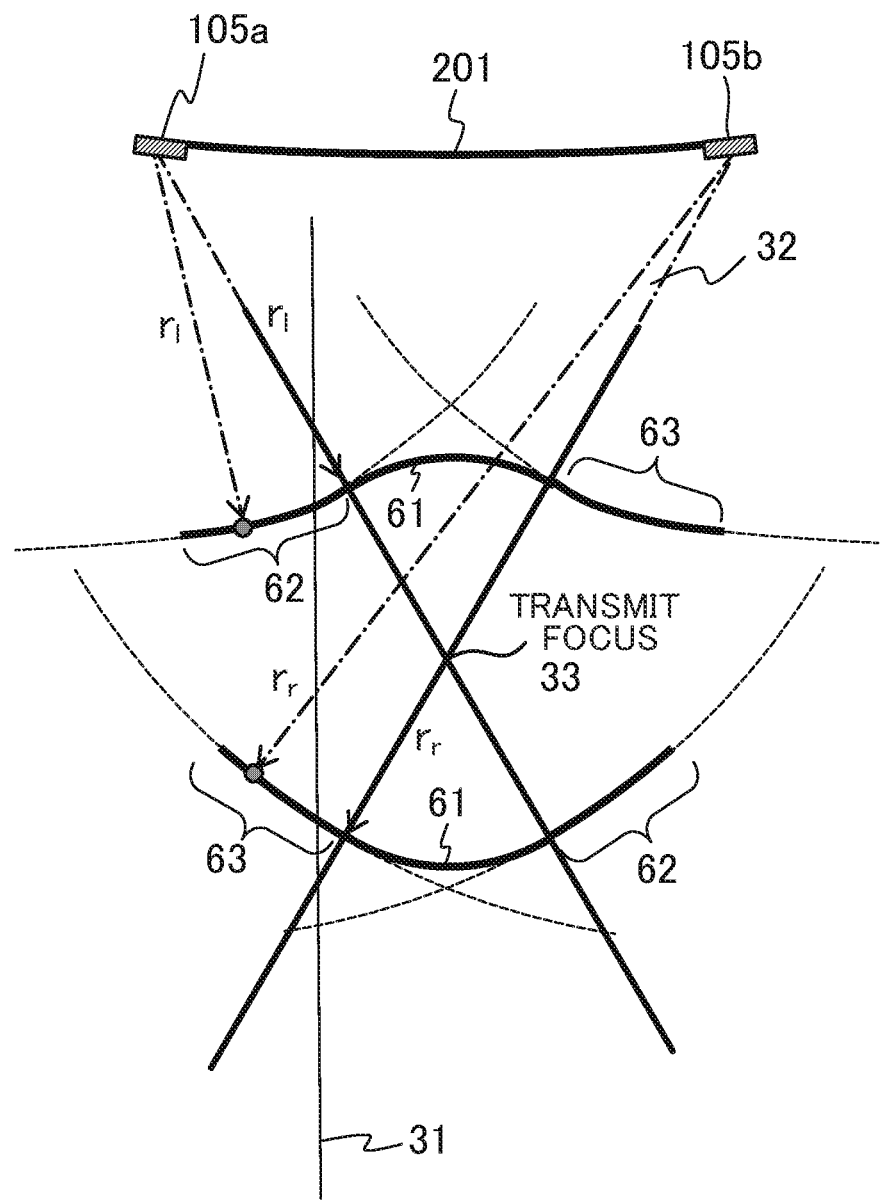
FIG. 6 is an explanatory diagram showing the shapes of wave fronts located inside of and outside of the irradiation area 32 of the focusing-type transmission beam.

However, as shown in FIG. 3(a), if plural reception scanning lines 31 are disposed in the entirety of the irradiation area 32 of the focusing-type transmission beam, an area B which passes through the outer side of the irradiation area 32 is generated in the first embodiment, as shown in FIG. 6, delay times outside of the irradiation area 32 are calculated under the assumption that spherical waves (diffracted waves) are propagated from ultrasound elements 105a and 105b at the ends of the transmission aperture 201 of the ultrasound element array 101 that transmits a transmission beam.

For example, as for an area on the left side of the irradiation area 32, it can be considered that a spherical wave (referred to as the diffracted wave hereinafter) 62 irradiated from the ultrasound element 105a at the left end is propagated in an area on the shallow side of a transmit focus 33, and it can also be considered that a spherical wave (referred to as the diffracted wave hereinafter) 63 irradiated from the ultrasound element 105b at the right end is propagated in an area on the deep side of the transmit focus 33. On the other hand, as for an area on the right side of the irradiation area 32, it can be considered that a diffracted wave 63 irradiated from the ultrasound element 105b at the right end is propagated in an area on the shallow side of the transmit focus 33, and it can also be considered that a diffracted wave 62 irradiated from the ultrasound element 105a at the left end is propagated in an area on the deep side of the transmit focus 33.

As shown in FIG. 6, the shape of a diffracted wave can be geometrically obtained. For example, in an area that is located on the shallow side of the transmit focus 33 and on the left side of the irradiation area 32, the shape of the diffracted wave 62 becomes a circular arc whose center is the ultrasound element 105a at the left end and whose radius is $r_l$. In an area that is located on the deep side of the transmit focus 33 and on the left side of the irradiation area 32, the shape of the diffracted wave 62 becomes a circular arc whose center is the ultrasound element 105b at the right end and whose radius is $r_r$. Therefore, in the area that is located on the left side of the irradiation area 32, the shape of the diffracted wave is switched from the diffracted wave 62 to the diffracted wave 63 with the vicinity of the transmit focus 33 as a boundary. In the area that is located on the right side of the irradiation area 32, the shape of the diffracted wave is switched from the diffracted wave 63 to the diffracted wave 62 with the vicinity of the transmit focus 33 as a boundary.

Therefore, in the case where a reception scanning line 31 is disposed as shown in FIG. 6 or FIG. 7(a), delay times calculated using the virtual source method are adapted to areas inside of the irradiation areas 32 of the transmission beam (the inner areas A and C), and the curve of the delay times is shown by a curve 71 in the inner area on the shallow side of the transmit focus 33 (near to the ultrasound element array 101), and shown by a curve 74 in the inner area C on the deep side of the transmit focus 33 as shown in FIG. 7(b) in addition, delay times generated by the diffracted wave 62 is shown by a curve 72 in an area B1, which is located on the shallow side of the transmit focus 33, of the outer area B, and delay times generated by the diffracted wave 63 is shown by a curve 73 in an area. B2, which is located on the deep side of the transmit focus 33, of the outer area B.

As is clear from FIG. 7(b), the curve 72 of delay times generated by the diffracted wave 62 and the curve 73 of delay times generated by the diffracted wave 63 do not contact each other, and therefore if these curves are adopted as they are, there arises a problem in that the delay times become discontinuous at the transmit focus 33 as shown by a solid line 82 in FIG. 8(a) (However, the discontinuity of the solid line 82 is shown by a straight line at the transmit focus 33 in FIG. 8). Unless this discontinuity of the delay times is changed into a kind of continuity using some kind of approximating curve or another, the pixel values of an ultrasound image to be generated become discontinuous in the vicinity of the depth of the transmit focus to generate an artifact Therefore, in this embodiment, the discontinuous variation between the delay times in the vicinity of the transmit focus is changed into a continuous variation using an appropriating approximating curve such as a curve 91 and a curve 92 shown in FIG. 9, or a curve 81 shown in FIG. 8(a), with the result that an artifact is prevented from occurring. However, these approximating curves 81, 91, or 92 has to have a complex shape including one or more inflection points in order to smoothly connect the two discontinuous curves.

For this purpose, although it is necessary to use delay times represented by the above approximating curve 81 or the like at the time of phasing of reception phasing points 5 disposed on the reception scanning line 31 in the external area B, if the lengths of segments 40b set in the outer area B are long, it becomes difficult to reflect the delay times represented by the approximating curve 81 or the like in delay times at the reception phasing points 5 calculated by interpolation calculation.

Figure 9:
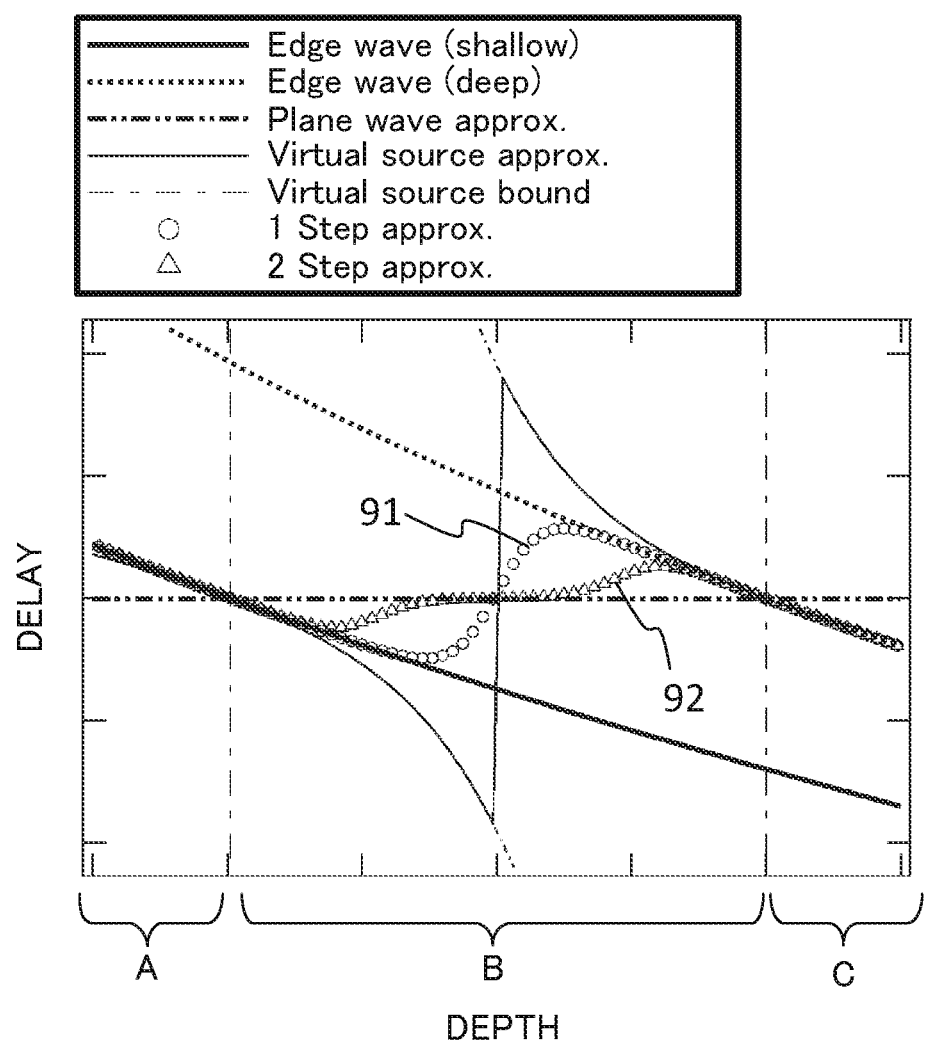
FIG. 9 is a graph showing the curves of delay times calculated from the wave fronts and examples of the shapes of approximating curves 91 and 92 that connect the curves of delay times.

Here, the offset parts of delay times caused by plane wave propagation are subtracted from delay times shown by the vertical axis in a graph shown in FIG. 7(b) or in a graph shown in FIG. 9. The offset parts of delay times caused by plane wave propagation are not subtracted from delay times in a graph shown in FIG. 8(a).

In the present invention, with the use of the configuration of the reception beamformer 108 shown in FIG. 1, the positions of the nodes of segments are changed in accordance with transmission conditions so that the delay times that complexly follow the changes in the vicinity of the transmit focus 33 can be set at the reception phasing points 5. In such a way, phased signals can be obtained using the continuous delay times even in the vicinity of the transmit focus outside of the irradiation area 32 of the transmission beam. As a result, an ultrasound image that is free from the deterioration of image quality in the vicinity of the transmit focus can be generated.

Hereinafter, the operations of the individual units of the reception beamformer 108 shown in FIG. 1 will be concretely explained with reference to FIG. 10. The segment setting unit 114 of the reception beamformer 108 divides equally the outer area B outside of the irradiation area 32 among the reception scanning lines 31 into segments with a predefined segment length to set plural segments. Plural segments, which have their segment lengths longer than the segment lengths of the segments set in the outer area B, are set in the inner areas A and C located inside of the irradiation area 32. Hereinafter, the above setting procedure will be explained in detail.

A segment length L1, which is transferred from the control unit 111, is set in the segment setting unit 114 (at step S1). A predefined value can be used as the segment length L1, or a value that is input by an operator via the console 110 can be used as the segment length L1.

The transmission profile calculation unit 113 receives transmission conditions for a transmission beam such as a transmission frequency and a transmission aperture from the control unit 11 (at step S2). The transmission profile calculation unit 113 calculates the irradiation area 32 of the transmission beam in the imaged area using the received transmission conditions (at step S3). In this case, the shape of the irradiation area 32 (hereinafter, also referred to as the transmission profile 32) can be calculated under the assumption that the shape is that of a combination of two triangles as shown in FIG. 3(a), or the transmission profile 32 can be calculated by performing a simulation under the assumption that there is detailed sound wave propagation or a nonlinear sound field as shown in FIG. 3(b).

The segment setting unit 114 receives the transmission profile 32 from the transmission profile calculation unit 113, and at the same time receives the positions of the reception scanning lines 31, which the transmission profile calculation unit 113 receives from the control unit 111, from the transmission profile calculation unit 113. Subsequently, the segment setting unit 114 calculates intersection points 34 between the transmission profile 32 and the reception scanning lines (at step S4). The segment setting unit 114 divides the reception scanning lines 31 into the inner areas A and C located inside of the transmission profile 32 and the outer area B located outside of the transmission profile 32 with the intersection points 34 as boundaries (at step S5).

The segment setting unit 114 disposes segment nodes 4b at the intersection points 34 as shown in FIG. 3(a) (at step S6). In the case where a segment node 4b cannot be disposed at an intersection point 34 because of a sampling frequency or the like, the segment node is disposed in the vicinity of the intersection point 34.

Next, the segment setting unit 114 divides the external area B equally into plural segments with their segment lengths L1 set at step S1, with the result that plural segments 40b are set (at step S7). Furthermore, the segment setting unit 114 divides the inner areas A and C equally into plural segments 40a and 40c with their segment lengths L2 that are longer than the segment lengths L1 of the outer area B, with the result that plural segments 40a and 40c are set in the inner areas A and C respectively. Herewith, as shown in FIG. 3(c), the segments 40b, whose segment length are shorter than the segment lengths of the segments in the inner areas A and C, can be set in the outer area B.

Here, a predefined value can be used as the segment length L2. In addition, the segment setting unit 114 can also calculate the segment length L2 in accordance with the number of segments set in the outer area B and the lengths of the inner areas A and C so that a total number of the segments set on the reception scanning line 31 is within a predefined range.

The segment setting unit 114 transfers the position information of the nodes 4a to 4c of the segments 40a to 40c in the respective areas to C to the delay time calculation unit 112. The delay time calculation unit 112 calculates a delay time at each of the positions of the segment nodes 4a to 4c on the basis of the preset shape of the delay time curve 81 or the like (at step S12). Because the segment lengths L1 in the outer area B are set short, the delay times at the segment nodes 4b have values that more accurately reflect the curve 81 of delay times with a predefined complex shape as shown in FIG. 11(b) in comparison with a case of a segment length being set short (FIG. 11(a)).

The segment setting unit 114 transfers a delay time and position information (or segment length information) for each of the calculated segment nodes 4a to 4c to the delaying/adding/phasing unit 204 (at step S13). This delay time and position information for each segment node are calculated for each ultrasound element 105 on each reception scanning line 31, and the calculated delay time and position information are transferred.

Figure 12:
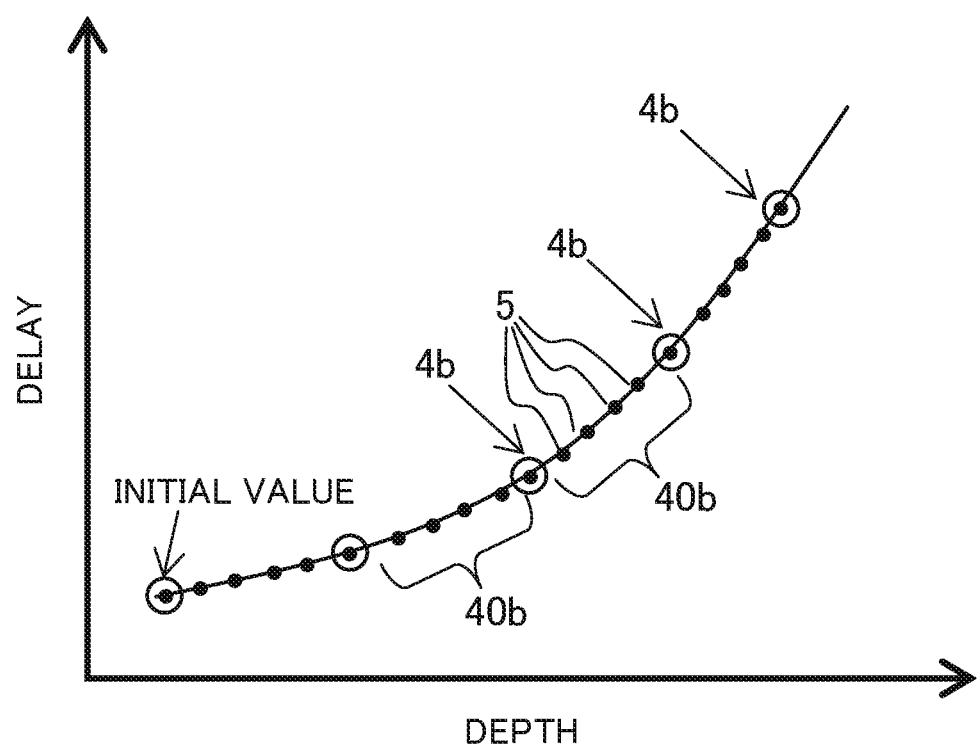
FIG. 12 is an explanatory diagram showing that delay times at reception phasing points 5 are calculated from, delay times at segment nodes using interval linear interpolation in the first embodiment.

The delaying/adding/phasing unit 204 calculates delay times at the positions of reception phasing points 5 in each of the segments 40a to 40c using interval linear interpolation calculation on the basis of the delay time and position information for each of the segment nodes 4a to 4c (Refer to FIG. 12). The delaying/adding/phasing unit 204 obtains phased signals regarding the reception phasing points 5 respectively after delaying and phasing the reception signals for the ultrasound elements 105, and then adding them, (at step S14). Because the segment lengths are set short in the outer area B, even if the delay times at the reception phasing points 5 are calculated by means of interval linear interpolation, the delay times of the complex curve 81 can be reflected. Furthermore, because the curve 81 of the delay times seldom vary drastically in the inner areas A and C, even if the segment length L2 is set longer than the segment length L1, the delay times at reception phasing points 5 can follow the curve 81.

The above steps S1 to S8 are executed regarding all the set reception scanning lines 31 for each transmission. Phased signals calculated at reception phasing points 5 of each reception scanning line 31 are stored in the beam memory 206. The above operation is repeated a predefined times while the irradiation position of the transmission beam is being changed. The inter-transmission synthesis unit 205 reads out plural phased signals at the same phasing point 5 from the beam memory 206, and, synthesizes the read-out phased signals. Using the synthesized phased signals, an image in the imaged area is generated. The generated image is stored in the frame memory 207, and at the same time it is output to the image processing unit 109. The image processing unit 109 displays the image, on which image processing is performed as required, on the image display unit 103. The displayed image does not generate a discontinuous artifact even in the vicinity of the transmit focus, and can display a highly accurate image.

Here, at step S6, as shown in FIG. 8(a), segment nodes 4b are disposed at intersection points 34 or in the vicinity of the intersection points 34. The advantageous effect of disposing the segment nodes 4b in such a way will be explained with reference to FIGS. 8(a) and (b) As shown in FIG. 8(a), because a curve, which the curve 81 approximates (asymptotically approaches), changes from the curve 71 to the curve 72 with an intersection point 34 as a turning point, and another curve, which the curve 81 approximates (asymptotically approaches), changes from the curve 74 to the curve 73 with another intersection point 34 as a turning point, the curve 81 has an inflection point at each of the two intersection points 34. Therefore, as shown in FIG. 8(b), in the case where segment nodes 4b are not disposed at the intersection points 34, disjunctions between line segments 85, which connect segment nodes 4a and 4c located in the inner areas A and C respectively with the segment nodes 4b in the outer area B, and the curve 81 become large. The fact that the disjunctions become large means that the delay times at the reception phasing points 5 do not follow the curve 81. Therefore, it is desirable to dispose the segment nodes 4b at the intersection points 34 as described in the above step S6.

In addition, when the transmission profile 32 is obtained by calculation at the above step S3, it is also possible to obtain the transmission profile 32 on the basis of the result of sound wave propagation calculation inside of a test object 100 based on transmission conditions as shown in FIG. 3(b). Herewith, the delay time profile itself can be accurately calculated, and reception beamforming compliant with realistic sound wave propagation can be executed. Therefore, an ultrasound image which has less deterioration of image quality in the vicinity of the depth of the transmit focus 33 can be generated.

Furthermore, in the case where the reception beamforming scheme is a nonlinear imaging scheme that utilizes nonlinear components of a sound wave, by calculating the transmission profile 32 that is made by the frequencies of the nonlinear components, which are used by the reception beamforming, within the frequency band of the transmission beam, it becomes possible to execute beamforming compliant with the realistic sound wave propagation in harmonic imaging, harmonic wave imaging and the like. Therefore, an ultrasound image which has less deterioration of image Quality in the vicinity of the depth of the transmit focus 33 can be generated.

Figure 10:
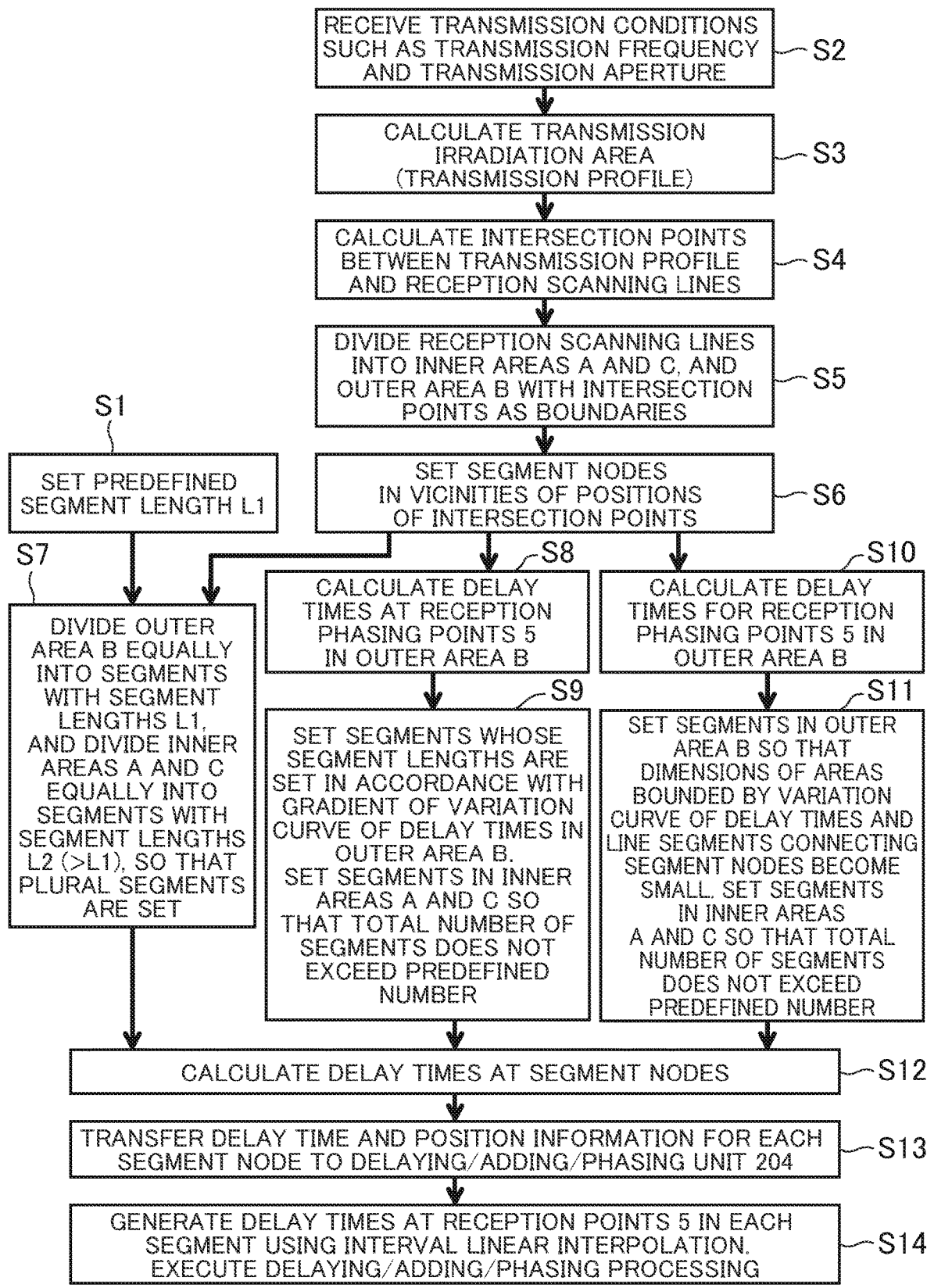
FIG. 10 is a flowchart showing a part of the operations of reception beamformers of the first to third embodiments.

In addition, although the procedures described in step 34 to step S7 shown in the abovementioned FIG. 10 are configured in such a way that the intersection points 34 between the transmission profile 32 and the reception scanning lines 31 are calculated (at step S4), the reception scanning lines 31 are divided into the areas A, B, and C after the segment nodes 4b are disposed at the intersection points 34, (at step S5), and the segments are disposed in the areas A, B, and C (at step S7), the present invention is not limited to these procedures. For example, the following configuration can also be conceivable in which, after the entirety of each of reception scanning lines 31 is divided into segments with their segment lengths L2 first, intersection points 34 between the transmission profile 32 and the reception scanning lines 31 are calculated, an outer area. B bounded by the intersection points 34 is calculated, and segments with their segment lengths L1 are newly disposed instead of segments with their segment lengths L2 only in the area B.

In this case, the calculation for obtaining the intersection points 34 can be executed with the use of the positions of the segment nodes 4 of segments with their segments length L2 set on all the reception scanning lines 31.

To put it concretely, as shown in FIG. 4(b), in the case where there is a boundary line outside of the transmission profile 32 in such a way that the boundary line crosses between the ith segment node 4(i) and the i−1th segment node 4 (i−1), an intersection 34 becomes an internally dividing point between the segment node 4(i) and the segment node 4 (i−1) as shown FIG. 4(b). Assuming that a formula representing the straight line of the transmission profile 32 is $a_{vs}x + B_{vs}z + C_{vs} = 0$ and that the coordinates of the segment node i is represented by $(x, z) = (x_i, z_i)$, a distance dseg1_new_node between the intersection point 34 and the segment node 4 (i−1) is given by Expression (2).

[Expression 2]

$$dseg1\_new\_node = \text{round}\left(dsegl[i] \times \frac{|a_{vs}x_{i-1} + b_{vs}z_{i-1} + c_{vs}|}{|a_{vs}x_i + b_{vs}z_i + c_{vs}|}\right) \quad (2)$$

The position of the intersection point 34 can be obtained using the distance from the segment node 4 (i−1) obtained from the abovementioned calculation. Herewith, the position of the intersection point 34 can be easily obtained from the coordinates of the two segment nodes.

Second Embodiment

An ultrasound image pickup apparatus of a second embodiment will be explained below.

In the second embodiment, a segment setting unit 114 makes a delay time calculation unit 112 calculate a delay time for each reception phasing point 5 in an outer area B located outside of an irradiation area 32 among reception scanning lines 31. Subsequently, a curve showing the relationship between the delay times obtained by the calculation and the positions of the reception phasing points 5 is calculated. The segment length of a segment in an area where the change (gradient) of the curve is large is set short, while the segment length of a segment in an area where the change (gradient) of the curve is small is set long.

The above procedure will be concretely explained with reference to FIG. 10. A transmission profile calculation unit 113 and the segment setting unit 114 calculates intersection points 34 between a transmission profile 32 and the reception scanning lines 31 as is the case of the first embodiment, and disposes segment nodes 4b at the intersection points 34 or in the vicinities of the intersection points 34 (at step S2 to step 6).

In the second embodiment the flow proceeds to step S8 after this, and the segment setting unit 114 transfers the position information of all the reception phasing points in the outer area B to the delay time calculation unit 112, makes the delay time calculation unit 112 calculate delay times for the respective reception phasing points 5, and receives the calculation result.

The flow proceeds to step S9, and the segment setting unit 114 calculates a curve (or an assembly of line segments) 131 that represents the relationship between the received delay times and the reception phasing points 5 as shown in FIG. 13(b). This curve (or this assembly of line segments) 131 corresponds to a predefined curve 81 of delay times. The segment setting unit 114 calculates the change (gradient) of the curve 131, and disposes segments each of which has a short segment length in areas where the change (gradient) is large, and disposes segments 40b each of which has a large segment length in areas where the change (gradient) is small as shown in FIG. 13(b). For example, segment lengths are predefined by the corresponding magnitudes of the gradient on a one-to-one basis, and this makes it possible to set segments in accordance with the magnitudes of the gradient Herewith, as shown in FIG. 13(b), segment nodes 4b are densely disposed on the steep parts of the gradient and segment nodes 4b are sparsely disposed on the gentle parts of the gradient, so that segment nodes 131 follow the curve 131.

Furthermore, the segment setting unit 114 calculates the number of segments disposed in inner areas A and C with reference to the number of the segments set in the outer area B so that a total number of segments set on the reception scanning line 31 does not exceed a predefined number, and determines segment lengths for the areas A and C on the basis of the lengths of the areas A and C respectively. The segment setting unit 114 sets segments 40a and segments 40c in the inner areas A and C respectively by equally dividing the inner areas A and C into segments whose segment lengths are equal to the calculated segment lengths respectively. Here, it is also conceivable that the segments 40a and 40c are set by equally dividing the inner areas A and C into segments whose segment lengths are predefined 12.

After the segments 40a to 40c are set in the areas A to C respectively, the delay time calculation unit 112 obtains delay times at the nodes of the segment 40a to 40c by calculation at step S12. Next, a delaying/adding/phasing unit 204 calculates delay times at reception phasing points within the segments of the respective areas using interval linear interpolation at step S13 and step S14. Because segment nodes are densely disposed on the steep parts of the gradient of the delay time curve 131 (81) as shown in FIG. 13(b) in the outer area B, delay times at reception phasing points 5 calculated using interval linear interpolation follow the shape of the delay time curve 131 (81).

Because other configurations are the same as those described in the first embodiment, explanations about those configurations will be omitted.

Even in the second embodiment, because delay times at reception phasing points 5 follow the shape of the complex curve 131 (81) of delay times in the vicinity of a transmit focus, a discontinuous artifact is not generated in the vicinity of a transmit focus in a displayed image, and a highly accurate image can be displayed.

Third Embodiment

An ultrasound image pickup apparatus of a third embodiment will be explained below.

In the third embodiment, a segment setting unit 114 makes a delay time calculation unit 112 calculate a delay time for each reception phasing point in an outer area B located outside of an irradiation area 32 among reception scanning lines 31. The segment setting unit 114 calculates a curve 131 showing the relationship between the obtained delay times and the positions of reception phasing points 5, and sets the nodes 4b of plural segments on the curve 131. Next, the segment setting unit 114 calculates plural line segments 132 that connect the set segment nodes 4b with straight lines. Next, the segment setting unit 114 calculates the dimensions of areas bounded by the curve 131 and the line segments 132, and adjusts the position of each of the nodes 4b of the plural segments (the segment length of each of the plural segments) respectively so that these dimensions become small.

The above procedure will be explained with reference to the flow shown in FIG. 10. A transmission profile calculation unit 113 and the segment setting unit 114 calculate intersection points 34 between the transmission profile 32 and the reception scanning lines 31, and dispose the segment nodes 4b at the intersection points 34 or in the vicinities of the intersection points 34 as is the case with the first embodiment (at step S2 to step S6).

In the third embodiment, the flow proceeds to step S8 after this, and the segment setting unit 114 transfers the position information of all the reception phasing points 5 in the outer area. B to the delay time calculation unit 112, makes the delay time calculation unit 112 calculate delay times at the respective reception phasing points 5, and receives the calculation result (at step S10).

The flow proceeds to step S11, and the segment setting unit 114 calculates a curve (or an assembly of line segments) 131 that represents the relationship between the received delay times and the reception phasing points 5 as shown in FIG. 13(a). This curve (or this assembly of line segments) 131 corresponds to a predefined curve 81 of delay times. The segment setting unit 114 disposes plural segment nodes 4b on the curve 131. The number of segment nodes 4b to be disposed can be a predefined number, or each of segment lengths 40b can be set as the segment length L1 used in the first embodiment. Alternatively, as is the case with the second embodiment, the segment length can be set according to the gradient of the curve 131.

The segment setting unit 114 calculates plural line segments 132 that connect the plural segment nodes 4b with straight lines. Next, the segment setting unit 114 calculates the sum of the dimensions of areas 133 bounded by the plural line segments and the curve 131. The segment setting unit 114 adjusts the position of each of the plural segment nodes 4b so that the sum of the dimensions of the areas 133 becomes a predefined value or smaller. In the case where the synthesis of the dimensions of the areas 133 does not become the predefined value or smaller even if the adjustment is executed, the number of the segment nodes 4b is increased. Herewith, as shown in FIG. 13(a), the segment nodes 4b that follows the change of the curve 131 can be set.

Furthermore, the segment setting unit 114 calculates the number of segments disposed in inner areas A and C in accordance with the number of segments set in the outer area B so that a total number of segments set on the reception scanning lines 31 does not exceed a predefined number, and determines the segment lengths of the segments in the areas A and C on the basis of the lengths of the areas A and C respectively. The segment setting unit 114 sets segments 40a and segments 40c in the inner areas A and C respectively by equally dividing the inner areas A and C into segments whose segment lengths are equal to the calculated segment lengths. Here, it is also conceivable that the segments 40a and 40c are set by equally dividing the inner areas A and C into segments whose segment lengths are predefined L2.

Because following steps 12 to 14 are the same as those described in the first and the second embodiments, descriptions of those steps will be omitted.

Although the delay times at the reception phasing point 5 in the segments 40b of the outer area B calculated at step S14 are calculated using interval linear interpolation, the segment nodes 4b follow the curve 131 thanks to the processes at steps S10 and S11, therefore the delay times at the reception phasing points 5 follow the shape of the curve 131 (81) of delay times. Therefore, a discontinuous artifact is not generated in the vicinity of a transmit focus in an image generated on the basis of phased signals, and a highly accurate image can be displayed.

Fourth Embodiment

In the first embodiment, it has been described using FIG. 4 (b) that a procedure can also be conceivable in which, after the entirety of each of reception scanning lines is divided into segments with their segment lengths equal to predefined L2 first, the intersection points 34 between transmission profile 32 and the reception scanning lines 31 are calculated, segment nodes 4 are disposed at the intersection points 34.

In that case, in FIG. 4(b) of the first embodiment, a new segment node I is disposed at the intersection point 34 between the ith segment node 4 (i) and the i−1th segment node 4 (i−1). However, instead of adding the new segment node 4, segment nodes located inside of inner areas A and C respectively can also be disposed at intersection points 34 by shifting them. This procedure will be explained using FIG. 14.

Figure 14:
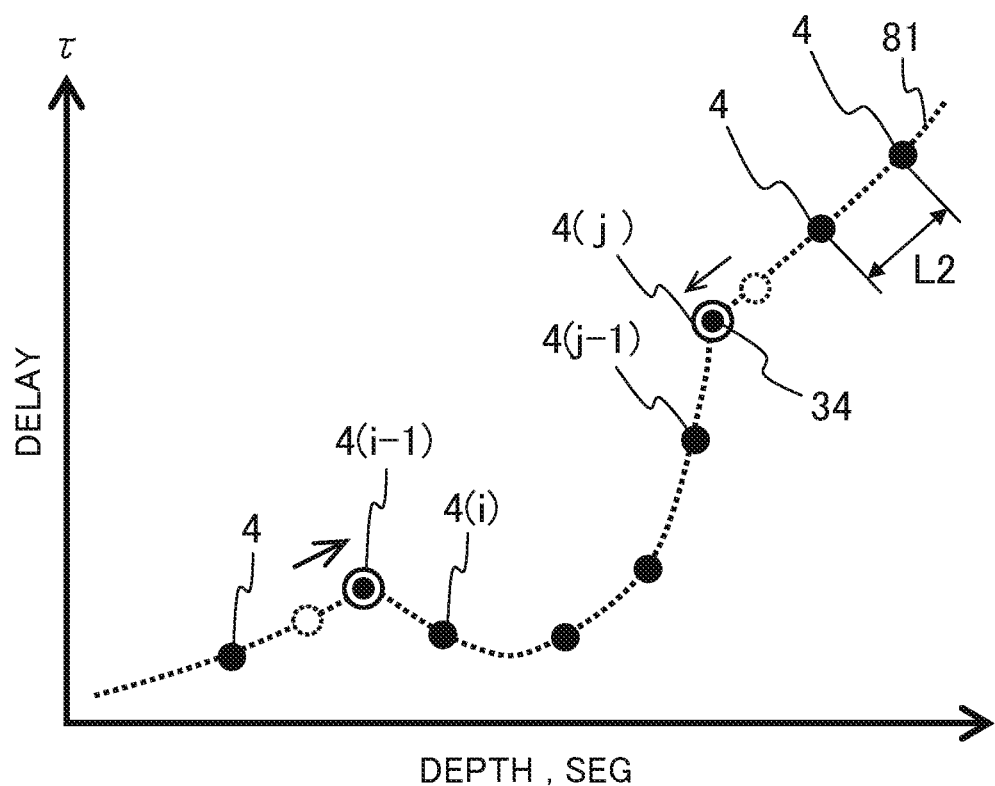
FIG. 14 is an explanatory diagram showing that segments nodes in inner areas A and C are shifted to intersection points 34 in a fourth embodiment.

As shown in FIG. 14, segment nodes 4 with their lengths L2 are disposed on the curve 81 of delay times. After the intersection points 34 are obtained by calculation as is the case with the first embodiment, the i−1th segment node 4 (i−1) located inside of the inner area A is shifted to an intersection point 34 on the boundary between the inner area A and an outer area B. In addition, the jth segment node 4(j) located inside of the inner area C is shifted to an intersection point 34 on the boundary between the outer area B and the inner area C. Herewith, the segments nodes are disposed at the intersection points 34.

In this manner, because shifting the segment nodes 4 located inside of the inner areas A and C respectively makes a distance between the segment node 4 at the intersection point 34 and a segment node 4 inside of the inner areas A and a distance between the segment node 4 at the intersection point 34 and a segment node 4 inside of the inner areas C longer than the segment length L2, the segment lengths of the segments set in the inner area A and in the inner area C respectively do not become shorter than the set length L2. Therefore, in the case where a total number of segments that can be disposed on the entirety of a reception scanning line 31 is predefined, more segment nodes can be disposed in the outer area B. This results in a merit that delay times at the reception phasing points 5 in the outer area B can follow the curve 81 more accurately.

Fifth Embodiment

Although, in order for the complex change of delay times in the outer area B located outside of the transmission profile 32 to be accurately followed, the description, in which the segment lengths in the outer area B are set shorter than those in other areas, has been made in the above-described first to fourth embodiments, there are some cases where the curve of delay times includes places where the gradient of the curve rapidly changes in the areas other than the outer area B. The segment division scheme of the present invention can be applied in a similar manner to places of the curve where the curve of delay times rapidly changes even if the places belong to any area. For example, it has been known that there is a place where the curve of delay times rapidly changes in front of a virtual focus point even in an inner area when the virtual source method is used, and the present invention can be applied even to such a place.

LIST OF REFERENCE SIGNS

100: Test Object
101: Ultrasound Element Array
102: Ultrasound Image Pickup Apparatus Body
103: Image Display Unit
104: Transmission Beamformer
106: Ultrasound Probe
107: Transmission/Reception Separation Circuit (T/R)
108: Reception Beamformer
709: Image Processing Unit
110: Console
111: Control Unit
112: Delay Time Calculation Unit
113: Transmission Area (Transmission Profile) Calculation Unit
114: Segment Setting Unit
204: Delaying (/Adding) /Phasing Unit

The invention claimed is:

1. An ultrasound image pickup apparatus comprising:
    an ultrasound element array in which a plurality of ultrasound elements are arranged in a predefined direction;
    a transmission beamformer configured to transmit a focusing-type transmission beam from a transmission aperture of the ultrasound element array to an imaged area of a test object; and
    a reception beamformer configured to delay reception signals output by the plurality of ultrasound elements, upon receiving ultrasound waves from the test object, by delay times to phase the reception signals, and outputs phased signals after adding the delayed and phased reception signals,
    wherein the reception beamformer includes at least one processor which is programmed to:
        calculate an irradiation area in the imaged area of the focusing-type transmission beam transmitted by the transmission beamformer;
    set a plurality of reception scanning lines, each of which includes a plurality of reception phasing points, in the imaged area, and divide each of the reception scanning lines into a plurality of segments and a plurality of nodes;
        calculate a plurality of first delay times at positions of the nodes of the segments using a predefined calculation method;
        calculate one or more second delay times at one or more of the reception phasing points included in each of the segments using the first delay times at the nodes of the segments; and
    delay the reception signals at the reception phasing points by the calculated second delay times
        wherein respective lengths of the plurality of segments are set in accordance with positional relationships between a shape of the calculated irradiation area and the scanning lines.

2. The ultrasound image pickup apparatus according to claim 1, wherein the reception beamformer includes the at least one processor which is further programmed to:
    calculate an outer area located outside of the irradiation area and an inner area located inside of the irradiation area among the reception scanning lines, and set the length of at least one segment among the segments in the outer area to be shorter than the length of at least one segment among the segments in the inner area.

3. The ultrasound image pickup apparatus according to claim 1, wherein the reception beamformer includes the at least one processor which is further programmed to:
    set the plurality of segments by equally dividing an outer area located outside of the irradiation area among the reception scanning lines into segments each of which has a predefined length, and setting the plurality of segments, having lengths longer than the predefined length of the segments in the outer area, in an inner area located inside of the irradiation area among the reception scanning lines.

4. The ultrasound image pickup apparatus according to claim 1, wherein a total number of the segments set on the reception scanning lines are within a predefined range.

5. The ultrasound image pickup apparatus according to claim 1, wherein the reception beamformer includes the at least one processor which is further programmed to:
calculate the second delay times at the respective reception phasing points located in an outer area located outside of the irradiation area among the reception scanning lines,
calculate a curve representing a relationship between the second delay times and positions of the reception phasing points, set the lengths of segments in first areas, in which a change of the curve is larger to be shorter than the lengths of segments in second areas in which the change of the curve is smaller.

6. The ultrasound image pickup apparatus according to claim 5, wherein a number of the segments set in the outer area is within a predefined range.

7. The ultrasound image pickup apparatus according to claim 1, wherein the reception beamformer includes the at least one processor which is further programmed to:
calculate the second delay times at the respective reception phasing points located in an outer area located outside of the irradiation area among the reception scanning lines,
calculate a curve representing a relationship between the second delay times and positions of the reception phasing points,
set the plurality of nodes of the segments on the curve,
calculate a plurality of line segments that connect the nodes of the segments with straight lines,
calculate dimensions of areas bounded by the curve and the line segments, and
adjust the lengths of the segments so that the dimensions are reduced.

8. The ultrasound image pickup apparatus according to claim 1, wherein the reception beamformer includes the at least one processor which is further programmed to:
calculate an outer area located outside of the irradiation area and an inner area located inside of the irradiation area among the reception scanning lines, and
set the nodes of the segments on boundaries between the outer area and the inner area.

9. The ultrasound image pickup apparatus according to claim 1, wherein the second delay times at the reception phasing points are calculated using linear interpolation calculation with reference to the first delay times at the nodes of the segments.

10. The ultrasound image pickup apparatus according to claim 1, wherein the reception beamformer includes the at least one processor which is further programmed to:
calculate the first delay times at the nodes of the segments located inside of the irradiation area among the reception scanning lines using a virtual source method, and calculates the first delay times at the nodes of the segments located outside of the irradiation area under an assumption that spherical waves are irradiated from the ultrasound elements at both ends of the transmission aperture.

11. The ultrasound image pickup apparatus according to claim 1,
wherein the reception beamformer includes a memory configured to store the the phased signals at each of the reception phasing points for each of the transmissions by the transmission beamformer and the at least one processor which is further programmed to:
select the phased signals regarding the same reception phasing point from the phased signals stored for the respective transmissions in the memory, and
synthesize the selected phased signals.

12. The ultrasound image pickup apparatus according to claim 1, wherein the shape of the irradiation area is calculated based on a result of a sound wave propagation calculation in an interior of a test object and a transmission condition of the transmission beam of the transmission beamformer.

13. The ultrasound image pickup apparatus according to claim 1,
wherein the reception beamformer includes at least one processor which is programmed to:
execute reception beamforming using nonlinear components of an acoustic wave; and
calculate an irradiation area for the frequencies of the nonlinear components used for the reception beamforming within a frequency band of the transmission beam.

* * * * *